United States Patent [19]

Ballschuh et al.

[11] 4,381,980
[45] May 3, 1983

[54] PROCESS FOR THE MANUFACTURE OF SULFOBETAINES

[75] Inventors: Detlef Ballschuh; Roland Ohme; Jochen Rusche; Horst Seibt; Kristina Geneis; Kurt Schaurich, all of Berlin, German Democratic Rep.

[73] Assignee: Akademie der Wissenschaften der DDR, Berlin, German Democratic Rep.

[21] Appl. No.: 281,457

[22] Filed: Jul. 8, 1981

[30] Foreign Application Priority Data

Jul. 11, 1980 [DD] German Democratic Rep. ... 222562

[51] Int. Cl.$^3$ ............ B01J 19/08; B01J 19/12; C07D 295/00
[52] U.S. Cl. ............ 204/158 R; 265/501.12; 544/158; 546/248; 204/158 HE
[58] Field of Search ........ 204/158 N, 158 T, 158 HE; 260/501.12; 544/158; 546/248

[56] References Cited

U.S. PATENT DOCUMENTS 2,959,617  11/1960  McKusik et al. ............... 204/158 N
4,238,609  12/1980  Mizuguchi et al. ................. 544/158
4,259,191  3/1981  Wagner ........................ 260/501.12

FOREIGN PATENT DOCUMENTS 965246  7/1964  United Kingdom ............... 544/158

*Primary Examiner*—Howard S. Williams
*Attorney, Agent, or Firm*—Jordan and Hamburg

[57] ABSTRACT

The invention relates to a process for the manufacture of N-substituted 3-sulfopropylammonium betaines.

N-substituted allylammonium compounds are reacted in the presence of initiators, such as oxygen, and catalytic acting transition metallic ions of the first, fifth, seventh or eighth secondary groups of the Periodic Table, with salts of sulfurous acid under mild reaction conditions.

The process can be executed with simple equipment and requires only small energy expenditures, the compounds of the present invention being produced selectively in an almost quantitative yield.

Further advantages of the process: the use of carcinogenic alkylates can be avoided, chemicals of technical purity and tap water can be employed and hardly any by-products result.

The substances have surface tension qualities and can be employed in many technical fields, especially in laundry agent formulations for energy-saving laundering processes.

26 Claims, No Drawings

PROCESS FOR THE MANUFACTURE OF SULFOBETAINES

BACKGROUND OF THE INVENTION AND PRIOR ART STATEMENT

The invention relates to a process for the manufacture of substituted 3-sulfopropyl ammonium betaines.

Examples of this class of compounds are used as components of laundry and cleaning agents since they exhibit excellent cleaning power at low temperatures in a suitable formulation; they are further employed as thermostable antistatic agents for molded masses of artificial material as well as coating material for textiles and woven fabrics. Sulfobetaines are also used as emulsifiers and as flotation agents. Good biological degrading ability is of special interest in the mentioned fields of application.

It has also been known to obtain sulfobetaines derived from 2-hydroxy-propane sulfonic acid through alkylation of tert. amines with 3-chloro-2-hydroxy-propane-1-sulfonic acid (DE-OS No. 24 31 031). The synthesis requires application of temperatures from 100° to 135° C., pressure, as well as the use of a considerable excess quantity of alkylation agent, wherein, however, yields of 75% average are obtained. The products are adulterated and difficult to crystallize. A further disadvantage of this synthesis process may be observed in the multistage synthesis of the required alkylation agent: glycerine-1.3-dichlorhydrin is obtained starting from allyl chloride, through the addition of HOCl, the epichlorhydrin from that and, ultimately, 3-chloro-2-hydroxy-propane-1-sulfonic acid through conversion with sodium sulfite. Therefore, this synthesis of sulfobetaine is not economical. Further, it has been known to produce sulfobetaines from tert. amines through alkylation with propane sultone (DE-AS No. 24 09 412). The propane sultone is obtained starting with allyl chloride by way of allylalcohol and 3-hydroxypropane-1-sulfonic acid as intermediates. Propane sultone is considered one of the most serious carcinogenic substances and its use, especially in synthesizing processes on a technical sale, requires special preventive measures (H. Druckrey, R. Preussman and collab., Z. Krebsforschung 75 (1970); 69; Registry of Toxic Effects of Chemical Substances, National Institute for Occupational Safety and Health, Maryland, U.S. (1975), 826).

In addition, it has been proposed (W. M. Linfield and colleag., J. Amer. Oil Chem. Soc. 53 (1976), 60; 55 (1978), 87) to add hydrogen sulfite to trialkylallylammonium salts for the synthesis of sulfobetaines of formula II. The conversion requires the simultaneous action of organic peroxide and hydrogen sulfite on allylammonium salts, wherein temperatures from 90° to 100° C. and reaction times of seven hours are required:

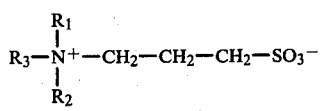

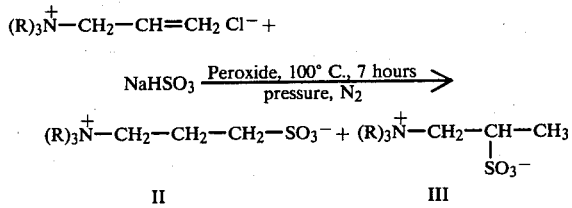

Care should be taken to exclude the oxygen from the air when rinsing the reaction mixture with nitrogen.

Other disadvantages of this sulfobetaine synthesis are the use of organic solvents, the long reaction times, as well as the mode of operation under pressure in autoclaves. The products obtained are not chemically uniform but comprise isomeric sulfobetaine III, besides the principal product II.

Moreover, additions of hydrogen sulfite radicals to unsubstituted olefins in the presence of peroxides have already been known from Houben-Weyl, vol. 9, page 380, This leads to yields of about 60%. In Houben-Weyl loc. cit. p. 382, chapter B, the statement is made in the example of the addition of hydrogen sulfite radicals to allyl alcohol that the use of catalytically acting heavy metallic ions in the presence of oxygen as opposed to the use of peroxides as catalysts results in an increase in yield by 50% besides other advantages. DE-OS No. 23 31 515 covers a corresponding process for the addition of hydrogen sulfite radicals to unsubstituted olefins, in which transition metals of the 1st, 7th and 8th secondary groups of the Periodic Table of the Elements are employed as catalysts in lieu of peroxides.

The olefins employed in this process, however, are not comparable with the trialkylammonium salts (positively substituted in the allyl position) of this invention since they are unsubstituted, i.e. contain double bonds (DE-OS No. 23 31 515) or are negatively substituted (Houben-Weyl, vol. 9, p. 382) and thus considerably differ from the allylammonium salts of the present invention concerning their electron configuration and reactivity.

SUMMARY OF THE INVENTION

It is the task of the present invention to avert the disadvantages of the known technical solutions and to develop a process for the manufacture of sulfobetaines in which the use of carcinogenic substances can be avoided, and which results in conceivably high yield by using mild reaction conditions, short reaction times and high selectivity.

The amount of organic waste products should be kept herein at a minimum.

This goal is achieved by a process for the production of the sulfobetaines of formula I, $$R_3-\underset{\underset{R_2}{|}}{\overset{\overset{R_1}{|}}{N^+}}-CH_2-CH_2-CH_2-SO_3^- \qquad I$$

in which $R_1$ represents hydrogen, straight chained or branched alkyl groups with 1-22 C atoms, hydroxyalkyl or aralkyl, $R_2$ is alkyl groups as cited for $R_1$; $R_1$ and $R_2$ may be equivalent or different or form a closed ring; and $R_3$ represents alkyl groups of the formula $CH_3-(CH_2)_{n-}$, where n=0 to 25, or branched alkyl groups or hydroxyalkyl groups or substituted alkyl groups, through conversion of trialkylallylammonium salts with hydrogen sulfite radicals, in which an allylammonium compound of the general formula IV according to the present invention

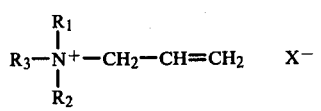

where $R_1$, $R_2$ and $R_3$ have the recognized definition and X represents a fluoride, a chloride, a bromide, a methosulfate or equivalent sulfate, sulfite or phosphate, is reacted with salts of sulfurous acid under thorough mixing, in solution at a pH value of 2-9 and at temperatures from 0° to 100° C., in the presence of initiators, and of ions of the transition metals of the first, fifth, seventh or eighth secondary group of the Periodic Table. It was found that in contrast to the relatively drastic reaction conditions (reaction operating under pressure, high temperatures, long reaction times) required in Linfield (J. Amer. Oil Chem. Soc. 53 (1976) 60; 1. c. 55 (1978) 87) for the conversion of allylammonium compounds with hydrogen sulfite radicals, hydrogen sulfite radical addition to allylammonium salts, in the presence of oxygen of air, occurs surprisingly easily by the process of the present invention and under mild conditions quantitatively, when traces of heavy metals are present, the pH range is from 2-9, preferably from 5-8. Only 1-sulfonate is selectively obtained herein, as can be established by $^{13}C$-nucleus-resonance-spectroscopy.

DETAILED DESCRIPTION OF PREFERRED EMBODIMENTS

The reaction is subject to a homogeneous catalysis by ions of transition metals of the 1st, 5th, 7th or 8th secondary group of the Periodic Table (for instance, $Cu^{++}$, $V^{5+}$, $Mn^{4+}$, $Fe^{+++}$, $Co^{++}$, $Ni^{++}$), following the same principles herein as understood from the oxidation of $SO_3^{2-}$ into $SO_4^{2-}$ in aqueous solution (A. Huss, J. Amer. Chem. Soc. 100 (1978), 19, 6252). The homogeneous catalysis requires extraordinarily low catalyst quantities; $10^{-4}$ gram atoms of any transition metal per liter are entirely sufficient since sulfite oxidation is still demonstrably catalyzed by $10^{-8}$ gram atom/liter. Under practical conditions—namely when workinng with technical chemicals and tap water in technical, metallic containers and arrangements—there are almost always sufficient quantities of $Fe^{+++}$, $Cu^{++}$ or $Ni^{++}$ disposed to trigger the catalysis effect. However, homogeneous catalysis may be excluded by blocking off the heavy metals (as sulfide, mercaptide) or through strong complex formation (ethylene-diamine-tetraacetic acid).

The metals to be catalyzed may be added as salts or oxides. Oxides are sufficiently dissolved in the $HSO_3^-$-containing reaction medium for homogeneous catalysis to be used. In this way it is possible to also use distinctly technical oxide compounds (as, for instance, lignite ashes) as catalysts. Even when the reaction medium is in contact with metallic Cu, Fe or Ni or in contact with alloys, it will pick up sufficient quantities of metallic ions to trigger the catalysis effect.

In a temperature range from 20°-40° C., a pH range of 5-8 is considered optimum. Then the reaction speed towards sulfobetaine is the greatest, while the secondary reaction of mere sulfite oxidation towards sulfate is minimal. The pH-range may be maintained through buffering or introducing $SO_2$. According to the invention, it is desirable to arrange for buffering by a mixture of alkali or ammonium hydrogen sulfite with alkali or ammonium sulfite. Besides maintaining the pH at an optimum level, the use of additional sulfite also compensates for the loss caused while simultaneous sulfate formation is being prepared.

In view of the consumption of the $HSO_3^-$, the formation of sulfobetaine results in an increase of the pH value; in contrast, the oxidation towards hydrogen sulfate radical results in a pH decrease so that the buffering strength of the reactive mixture need not be great. The addition of the hydrogen sulfite radical to the allylammonium group is made exclusively as anti-Markovnikov addition to 1-sulfonate over a sulfite anion radical as an intermediate step, which is formed after equation 1 (in a homogeneous catalysis by $Cu^{++}$):

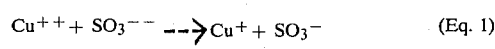   (Eq. 1)

(Eq. 2)

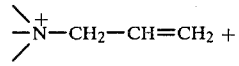

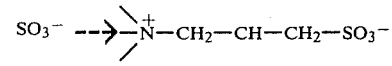

(Eq. 3)

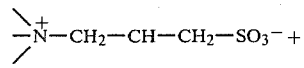

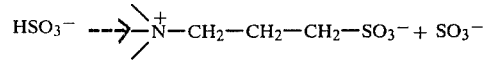

   (Eq. 4)

In Equation 2, the sulfite anion radical is added to the allylammonium group, forming a sulfobetaine radical which reacts with the hydrogen sulfite anion of Equation 3—present in large quantities in the buffering range—to a sulfobetaine. The resultant sulfite anion radical continues the reaction according to Equation 2 so that the formation of sulfobetaine proceeds in the sense of a radical chain reaction. Oxygen from air regenerates the homogeneous catalyst $Cu^{++}$ according to Equation 4. Therefore, oxygen is also needed only in catalytic quantities so that slow air introduction is sufficient to continue sulfobetaine formation; absence of oxygen will, however, interrupt the reaction. Instead of oxygen, the reaction may also be initiated with traditional radical initiators, for instance ammonium persulfate, hydrogen peroxide, by organic peroxides or hydroperoxides or through nitrates or nitrites. This operating procedure as a rule, does not result in advantages because of the greater expenditures involved; however, the use of initiators may be of advantage when operating with foaming reaction mixtures. Also the simultaneous introduction of radical initiators and limited oxygen quantities may be of advantage when foaming substrates without anti-foam additives are to be prepared. Also, initiation by UV or gamma rays is possible.

According to the invention, aqueous solutions may be used. It will be desirable to proceed in a manner so that the solution of allyl ammonium compound and the hydrogen sulfite buffer solution too are gradually added at the same time.

Water-alcohol mixtures may be used when the solubility qualities of allylammonium salts so require, wherein tert butanol or 2-propanol are especially suitable. In long-chained compounds with high surface tension, foam formation may be counteracted by using alcohol-containing solutions. For example, the 2-propanol:water ratio may be 70:30, without the sulfite and hydrogen sulfite becoming insoluble. In the synthesis of strongly foaming sulfobetaines, it may, moreover, be advantageous in individual cases to lower the stirring speed and aeration and to introduce oxygen in low amounts instead of in an air stream.

One may also operate at higher temperatures if the solubility characteristics of the allyl ammonium salts so require; in these cases the optimal pH range is expanded downwardly.

The allyl ammonium salts required for a sulfobetaine synthesis,

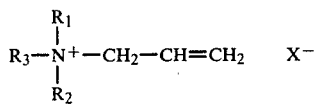

are obtained by incremental alkylations, wherein, as a rule, the much larger $R_3$ group or the allyl group is introduced in the last reaction step.

The alkyl group $R_3$ in formulas I and IV may be substituted. The substituent in $R_3$ herein may be an aminoalkyl, a carbonic acid amide, a fluorocarbonic acid amide, a carbonic acid ester or a sulfonic amide group. The carbonic acid amide groups or fluorocarbonamide groups may have the following structure:

$$R_4-CH_2-CO-NR_5-(CH_2)_r-,$$

where $r=0$ to 3, or $$C_mF_{2m+1}-CO-NR_5-(CH_2)_r-,$$

where $m=1$ to 12 or $r=0$ to 3, or $$CH_2=CH-(CH_2)_p-CO-NR_5-CH_2-CH_2-,$$

where $p=0$ to 13, wherein $R_4$ and $R_5$ may have the same definition as $R_1$ in formula I or formula IV.

Carbonic acid ester groups of the following structures are possible:

$$R_4-CH_2-COO-(CH_2)_2-$$

or $$CH_2=CH-(CH_2)_q-COO-(CH_2)_2-,$$

where $q=0$ to 13, and wherein $R_4$ has the definition as $R_1$.

If a sulfonic amide group is available as a substituent in $R_3$, structures such as $$R_4-CH_2-SO_2-NR_5-(CH_2)_r-,$$

where $r=0$ to 3, or $$R_4-C_6H_4-SO_2-NR_5-(CH_2)_r-,$$

where $r=0$ to 3, are possible. $R_4$ and $R_5$ then have the definition of $R_1$. Aminoalkyl groups of the structure $$R_4-CH_2-NH-(CH_2)_r-,$$

where $r=0-3$, are possible.

When $R_1$ and $R_2$ form a closed ring, the ring may have the structure or piperidinium or of morpholinium. The advantages of the process of this invention consist in that the reaction can be processed under mild conditions and, for this reason, power consumption is minimal;
it is possible to use technically pure starting substances;
it is possible to avoid the use of carcinogenous alkylates;
the conversion can be made by using relatively simple equipment;
the reaction times are short, and
selectivity in the reaction is very good and, thus, the yield is very high.

EXAMPLES

EXAMPLE 1

3-sulfopropyltrimethylammonium-betaine
$R_1=R_2=R_3=CH_3$ in the general formula I 1.26 g (0.01 mol) sodium sulfite ($Na_2SO_3$) are dissolved in 60 ml tap water in a sulfonation flask with a stirrer, thermometer and gas inlet tube. Then, two aqueous solutions of 45 ml each are prepared; one is derived from 13.55 g (0.1 mol) trimethylallylammonium chloride dissolved in tap water; the other one from 9.5 g (0.05 mol) $Na_2S_2O_5$ and 6.3 g (0.05 mol) $Na_2SO_3$ dissolved in tap water. The prepared solutions are simultaneously dripped with stirring and simultaneously passing air therethrough during a period of one hour, wherein the temperature of the reaction mixture increases by 8.5° C. During conversion, the pH-value remains in the 7 range. Lowering of the temperature indicates the end of the reaction after a post-reaction time of 15 minutes. Conversion at this time is quantitative, as can be established by $^1H$-NMR-spectroscopy with the vanishing of the allyl protons signals.

After the reaction solution is dried in the drier, sulfobetaine is obtained as a colorless, crystalline substance in mixture with sodium sulfite, sodium sulfate and sodium chloride from which betaine cannot be extracted. The product is obtained salt-free by ion exchange. Melting point: 325° C. (decomposition). The tap water used for preparing the reaction solutions contains $2 \cdot 10^{-6}$ gram atom Fe/l. Distillated water may be employed instead of tap water, if one adds homogeneous catalysts as transitional metallic ions.

The product exhibits the following $^{13}C$-NMR spectrum ($D_2O$, external standard TMS); the figures provided with the atomic symbols correspond to the chemical displacements in ppm:

$^x$Signal splitting through $^{14}N$ quadrupole moment.

$^1H$-NMR-spectrum in $D_2O$; internal standard sodium trimethylsilylpropane sulfonate (TMSPS). Chemical displacements, $\tau$ values in ppm: s: 6.82; N—$CH_3$; m: 6.3–8.1 sulfopropyl group.

The NMR spectra are completely identical with the spectra of a comparable product obtained from trimethylamine and propane sultone.

EXAMPLE 2

3-sulfopropyltriethylammoniumbetaine
$R_1=R_2=R_3=C_2H_5$ in the general formula I One proceeds as described in Example I, using 17.75 g (0.1 mol) triethylallylammonium chloride as a trialkylallylammonium compound.

Quantitative conversion.
Melting point: 287°–290° C.

The product exhibits the following $^{13}$C-NMR-spectrum (D$_2$O, external standard TMS); the figures provided with the atomic symbols correspond to the chemical displacements in ppm:

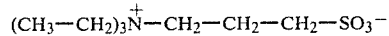

$$\underset{8.2\quad 56.25^x\quad 54.2\quad 18.8\quad 48.8}{(CH_3-CH_2)_3\overset{+}{N}-CH_2-CH_2-CH_2-SO_3^-}$$

$^x$Signal splitting through $^{14}$N quadrupole moment.

$^1$H-NMR spectrum (data information as in example 1): t: 8.7; J = 7 Hz (CH$_3$); q: 6.67; J = 7 Hz—CH$_2$—; m: 6.3–8.2 sulfopropyl group.

The NMR spectra are completely identical with the spectra of a comparable product obtained from triethylamine and propane sultone.

EXAMPLE 3

3-sulfopropyldimethylammoniumbetaine
$R_1 = R_2 = CH_3$; $R_3 = H$ in the general formula I One proceeds as described in Example 1, using as alkylallylammonium compound 12.16 g (0.1 mol) dimethylallylamine hydrochloride.
Quantitative conversion.
Melting point: 210° C.

The product exhibits the following $^{13}$C-NMR spectrum (data as above):

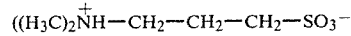

$$\underset{44.3^x\qquad 57.7^x\quad 21.4\quad 49.2}{((H_3C)_2\overset{+}{N}H-CH_2-CH_2-CH_2-SO_3^-)}$$

$^x$Signal splitting through $^{14}$N—quadrupole moment.

$^1$H-NMR spectrum (details as before): s: 7.08; N—CH$_3$; m: 7.5–8.2 —CH$_2$—; m: 6.4–7.3 N—CH$_2$—, $^-$O$_3$S—CH$_2$—.

The NMR spectra are identical with the spectra of a comparable product prepared from dimethyl amine and propane sultone.

EXAMPLE 4

3-sulfopropyl-dimethyl-n-dodecylammonium betaine $R_1 = R_2 = CH_3$ $R_3 = n$—C$_{12}$H$_{25}$ in the general formula I Dimethyl-n-dodecyl-allylammonium chloride was produced by the alkylation of dimethyldodecylamine with allyl chloride with heating in the presence of water.

The water used in this experiment had 10$^{-5}$ gram atom Cu$^{++}$/1. The following three solutions are prepared with this water:
1. 1160 g of a 25% solution of dimethyl-dodecylallylammonium chloride (1 mol);
2. 95 g (0.5 mol) sodium metabisulfite and 63 g sodium sulfite are dissolved to make a solution of 1160 g; and
3. 12.6 g sodium sulfite (0.1 mol) are dissolved in 200 ml water.

The solution as per 3 above is put inside a sulfonation flask provided with a stirrer, dripping funnel, gas-inlet tube and thermometer. Solution 1 and solution 2 are then dripped out simultaneously from two dripping funnels during a time span of 90 minutes, starting with an initial temperature of 24° C. Air is permitted inside the flask during the dripping and a white, milky emulsion of air bubbles is produced through heavy stirring, in order to achieve a conceivably fine distribution of the oxygen. Since the reaction mixture herein foams heavily, foam formation is curbed through the addition of isopropanol. Temperature increases during dripping by approximately 10° C.; the pH-value remains around 7 during the conversion. After the temperature decreases, stirring is continued for about 30 minutes. The conversion is now quantitative ($^1$H-NMR spectroscopically ascertained). After evaporation of the solvent, sulfobetaine is obtained in a mixture with sodium salts of the remaining sulfite, sulfate and chloride. Through extraction with ethanol, the sulfobetaine can be quantitatively separated from the salts.

Melting point: 209° C.

The product obtained is identical with a comparable substance obtained from dimethyl dodecylamine with propane sultone.

EXAMPLE 5

3-sulfopropyl-dimethyl-iso-tetradecylammonium betaine (technical mixture with C$_{10}$–C$_{18}$ group as the longest substituents)

In formula I: $R_1 = R_2 = CH_3$, $R_3$ = average chain length i-C$_{14}$H$_{29}$.

Iso-C$_{14}$H$_{29}$N (CH$_3$)$_2$ was obtained through chlorination of the hydrocarbons C$_{10}$–C$_{18}$ (from the Parex process) and transformation of the branched alkylchloride mixture with dimethylamine; subsequent quarternization with allyl chloride resulted in a 42% aqueous iso-alkyl-dimethylallylammonium chloride solution; the experiment was conducted in tap water.

The following three solutions are prepared:
1. 755 g (1 mol) 42% iso-tetradecyldimethylallylammonium chloride solution;
2. 95 g (0.5 mol) sodium metabisulfite and 63 g (0.5 mol) sodium sulfite are dissolved in tap water to make a 755 g solution; and
3. 12.6 g sodium sulfite (0.1 mol) are dissolved in 200 ml tap water.

One proceeds as described in Example 4 and drips solution 1 and solution 2 in the course of one hour into solution 3. It is not necessary to add an anti-foaming agent. Conversion is quantitative. A non-crystallizing sulfobetaine mixture is obtained after evaporation of the solvent, which is separated by extraction with ethanol.

EXAMPLE 6

3-sulfopropyl-dimethyl-n-tetradecylammonium betaine $R_1 = R_2 = CH_3$, $R_3 = n$—C$_{14}$H$_{29}$ in the general formula I Dimethyl-n-tetradecyl-allylammonium bromide was obtained by reacting dimethylallylamine with n-tetradecyl bromide, which, as in the previous examples, was converted into sulfobetaine. Here, Mn$^{++}$ was used as a homogeneous catalyst (10$^{-4}$ gram atom Mn$^{++}$/1).

The conversion was quantitative.
Melting point: from 125° on decomposition.

The product exhibits the following $^{13}$C-NMR spectrum (indications as above):

$$\underset{6.9\quad 15.3\quad 30.6\quad 67.1^x\quad 54.2;53.3\,67.2^x\qquad 49.9}{CH_3-CH_2-(CH_2)_{11}-CH_2-\overset{+}{N}(CH_3)_2-CH_2-CH_2-CH_2-SO_3^-}$$

-continued

ˣchemical displacements may also be rearranged.

EXAMPLE 7

3-sulfopropyl-dimethyl-n-hexadecylammonium betaine $R_1=R_2=CH_3$ $R_3=C_{16}H_{33}$— in the general formula I Dimethyl-n-hexadecyl-allyl-ammonium chloride was converted into sulfobetaine in the same manner as in the previous examples, however the ratio of the reacting components was allylammonium salts:hydrogen sulfite:-sulfite=1:1:0.1. The dosage of the components was made dependent on the pH-value for each, measured electrically, to maintain the pH value of the reaction mixture around 7. In this way, the sulfite excess may be decreased. $10^{-4}$ gram atom $Fe^{++}/1$ (added as sulfate) was used as a catalyst.

Melting point: 108° C.

The product is identical with a comparable product obtained from dimethylhexadecylamine and propane sultone.

EXAMPLE 8

Sulfobetaine mixture $C_{16}$–$C_{18}$ 3-sulfopropyl-dimethyl-n-hexadecyl-ammoniumbetaine
and
3-sulfopropyl-dimethyl-n-octadecyl-ammoniumbetaine $R_1=R_2=CH_3$, $R_3=C_{16}H_{33}$ and $C_{18}H_{37}$ in the general formula I The mixture of alkyldimethylallylammonium salts was obtained from alkyldimethylamines through conversion with allylchloride in water. The ratio $C_{16}/C_{18}$ was 1:1.

The mixture of 0.5 mol of each of the above alkylammonium salts, in the form of a 10% aqueous solution, was converted into the corresponding sulfobetaine mixture as described in the preceding examples. Isopropyl alcohol was employed to the extent necessary as an anti-foaming agent. The sulfobetaine mixture is slightly water-soluble and precipitates from the reaction mixture during conversion.

As in above examples, conversion is quantitative.
Melting point: 102°–106° C.

EXAMPLE 9

3-sulfopropyl-dimethyl-2-acetamidoethyl-ammonium betaine $R_1=R_2=CH_3$; $R_3=CH_3CO$—NH—$CH_2CH_2$—in the general formula I The starting allyl compound is formed by initially converting ethyl acetate with N,N-dimethylethylene diamine into amide and then quarternizing with allyl halide. One proceeds as described in Example 1, using the above amide as an allylammonium compound.

Conversion is quantitative.
Melting point: starting from 190° C. (decomposition).

EXAMPLE 10

3-sulfopropyl-dimethyl-2-tetradecanoylamidoethyl-ammonium betaine $R_1=R_2=CH_3$;
$R_3=C_{13}H_{27}$—CO—NH—$CH_2$—$CH_2$—in the general formula I The starting allyl compound is formed by initially reacting myristic acid methyl ester with N,N-dimethylethylenediamine to form an amide, and subsequently quarternizing with an allyl halide. One proceeds as described in Example 4, however using tap water instead of copper ions to produce the reaction mixture. A quantitative yield of sulfobetaine is obtained (melting point: 58° C.) from the concentrated reaction mixture extracted by alcohol.

The product exhibits the following $^{13}$C-NMR spectrum (data as above):

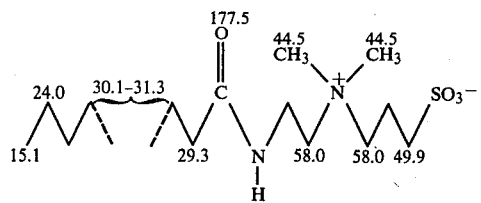

non-attributable signals: 44.8 and 33.3 ppm.

The NMR spectrum is identical with that of a product produced from propane sultone.

EXAMPLE 11

3-sulfopropyl-dimethyl-hexadecanoylamidoethyl-ammonium betaine

The starting compound is produced by reacting a palmitic acid methylester with N,N-dimethylenediamine to form an amide which is converted into an allyl.

One proceeds in the manner described in Example 4, however using 0.9 mg $MnO_2$/liter reaction mixture ($10^{-5}$ gram atom MnII) as a catalyst instead of $Cu^{++}$. Quantitative conversion.

Melting point: 85° C.

OTHER EXAMPLES

By the same methods described in the preceding examples, the allylized amides of the N,N-dimethylethylenediamine of oleic acid, of perfluorine octane acid, of the 4-alkylbenzenesulfonic acids, of the alkylsulfonic acids and of the undecylenic acids may be converted into the corresponding sulfobetaines.

We claim:
1. A process for preparing a sulfobetaine of formula I

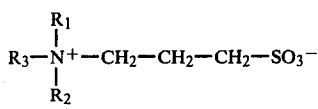

wherein
$R_1$ is hydrogen, straight-chained or branched alkyl groups of 1 to 22 carbon atoms, hydroxyalkyl, or aralkyl, $R_2$ is an alkyl group as indicated for $R_1$, provided that $R_1$ and $R_2$ may be the same or different or together form a closed ring, and $R_3$ is an alkyl group of the formula $CH_3—(CH_2)_n—$ where n=0 to 25 branched alkyl groups, hydroxyalkyl groups, or substituted alkyl groups, wherein an alkylammonium salt of the general formula IV $$R_3-\overset{R_1}{\underset{R_2}{N^+}}-CH_2-CH=CH_2 \quad X^- \qquad IV$$

wherein $R_1$, $R_2$ and $R_3$ have the same definition as above, and X is fluoride, chloride, bromide, methosulfate or an equivalent sulfate, equivalent sulfite, and equivalent phosphate, is reacted with at least one salt of sulfurous acid, in a solution at a pH of 2-9, at a temperature from 0° C. to 100° C., and in the presence of at least one transition metal ion of the first, fifth, seventh, or eighth secondary group of the Periodic Table of the Elements and at least one initiator.

2. The process of claim 1 wherein the addition of a hydrogen sulfite radical to the compound of formula IV to form the compound of formula I is anti-Markovnikov addition as follows:

$$\overset{\diagdown}{\underset{\diagup}{N^+}}-CH_2-CH=CH_2 + SO_3^-$$

$$\dashrightarrow \overset{\diagdown}{\underset{\diagup}{N^+}}-CH_2-CH-CH_2-SO_3^-$$

$$\overset{\diagdown}{\underset{\diagup}{N^+}}-CH_2-CH-CH_2-SO_3^- + HSO_3^-$$

$$\dashrightarrow \overset{\diagdown}{\underset{\diagup}{N^+}}-CH_2-CH_2-CH_2-SO_3^- + SO_3^-.$$

3. The process of claim 2 wherein the pH is from 5-8.

4. The process of claim 3 wherein the solvent is selected from the group consisting of water, alcohol, and mixtures thereof.

5. The process of claim 4 wherein the alcohol is selected from the group consisting of methanol, ethanol, tertiary butanol, 2-propanol, and mixtures thereof.

6. The process of claim 5 wherein said initiator is air.

7. The process of claim 5 wherein said initiator is substantially pure oxygen.

8. The process of claim 5 wherein said initiator is at least one salt of peroxy disulfuric acid.

9. The process of claim 5 wherein said initiator is ultra-violet rays.

10. The process of claim 5 wherein said initiator is gamma rays.

11. The process of claim 5 wherein the transition metal ions are present in a concentration of from $10^{-8}$ to $10^{-3}$ gram atom/liter.

12. The process of claim 11 wherein the transition metal ions are selected from the group consisting of copper, vanadium, manganese, iron, cobalt, nickel and mixtures thereof.

13. The process of claim 12 wherein said transition metal ions are introduced into solution in a composition selected from the group consisting of metallic salts, metallic oxides, free metal form, and mixtures thereof.

14. The process of claim 13 wherein said transition metal ions are introduced into solution through technically pure chemicals.

15. The process of claim 13 wherein said transition metal ions are introduced into solution through tap water.

16. The process of claim 13 wherein said transition metal ions are introduced into solution through metallic apparatuses.

17. The process of claim 13 wherein said salt of sulfurous acid is selected from the group consisting of alkali salts, magnesium salts, ammonium salts, and mixtures thereof.

18. The process of claim 17 wherein the temperature is from 20° C. to 40° C.

19. The process of claim 18 wherein said salt of sulfurous acid is added in a medium selected from the group consisting of hydrogen sulfite solutions, disulfites, and mixtures thereof.

20. The process of claim 19 wherein sulfurous acid is added in a molar ratio to a slight molar excess of the allyl ammonium compound of the general formula IV.

21. The process of claim 20, additionally comprising a buffering system.

22. The process of claim 21 wherein $HSO_3^-/SO_3^{2-}$ mixtures are the buffering system.

23. The process of claim 22 which is supplemented by additional sulfur dioxide to maintain the pH.

24. The process of claim 23 wherein the allyl ammonium compound of the general formula IV and the sulfurous acid salt are gradually mixed together in solution over a period of time.

25. The process of claim 24 wherein $R_3$ has at least one of the following structures:

$$R_4-CH_2-CO-NR_5-(CH_2)_r-,$$

where r=0 to 3, or $$C_mF_{2m+1}-CO-NR_5-(CH_2)_r-,$$

where m=1 to 12 and where r=0 to 3, $$CH_2=CH-(CH_2)_p-CO-NR_5-CH_2-CH_2-,$$

where p=0 to 13, $$R_4-CH_2-COO-(CH_2)_2-, \text{ or}$$

$$CH_2=CH-(CH_2)_q-COO-(CH_2)_2-,$$

where q=0 to 13, $$R_4-CH_2-SO_2-NR_5-(CH_2)_r-,$$

where r=0 to 3, or $$R_4-C_6H_4-SO_2-NR_5-(CH_2)_r-,$$

where r=0 to 3, $$R_4-CH_2-NH-(CH_2)_r-,$$

where r=0 to 3, wherein $R_4$ and $R_5$ have the same definition as $R_1$.

26. The process of claim 25 wherein $R_1$ and $R_2$ form a closed ring structure selected from the group consisting of piperidinium, morpholinium, and mixtures thereof.

* * * * *